(12) United States Patent
Tuan et al.

(10) Patent No.: US 8,052,787 B2
(45) Date of Patent: Nov. 8, 2011

(54) BIO-MATERIAL AND METHOD OF PREPARATION THEREOF

(75) Inventors: Wei-Hsing Tuan, Taipei (TW); Yueh-Han Lee, Taipei (TW); Hsueh-Hui Kuo, Taipei (TW)

(73) Assignee: National Taiwan University, Taipei (TW)

(*) Notice: Subject to any disclaimer, the term of this patent is extended or adjusted under 35 U.S.C. 154(b) by 539 days.

(21) Appl. No.: 12/235,855

(22) Filed: Sep. 23, 2008

(65) Prior Publication Data

US 2009/0088311 A1 Apr. 2, 2009

(30) Foreign Application Priority Data

Sep. 28, 2007 (TW) .............................. 96136125 A

(51) Int. Cl.
*C08L 5/00* (2006.01)
*C08L 5/12* (2006.01)
*A61F 2/28* (2006.01)
(52) U.S. Cl. ................ 106/205.2; 106/205.9; 623/23.56
(58) Field of Classification Search ................ 106/205.2, 106/205.9; 623/23.56
See application file for complete search history.

(56) References Cited

U.S. PATENT DOCUMENTS

| 3,443,261 | A | * | 5/1969 | Cruz, Jr. et al. | 623/23.61 |
| 4,264,493 | A | * | 4/1981 | Battista | 530/354 |
| 5,180,426 | A | * | 1/1993 | Sumita | 106/35 |
| 6,949,251 | B2 | * | 9/2005 | Dalal et al. | 424/423 |
| 7,722,895 | B1 | * | 5/2010 | McKay et al. | 424/423 |
| 7,754,246 | B2 | * | 7/2010 | Moseley et al. | 424/602 |
| 2004/0185021 | A1 | * | 9/2004 | Hubbard | 424/70.13 |
| 2005/0074415 | A1 | * | 4/2005 | Chow et al. | 424/49 |
| 2006/0225621 | A1 | * | 10/2006 | Insley et al. | 106/691 |

* cited by examiner

*Primary Examiner* — David M Brunsman
(74) *Attorney, Agent, or Firm* — Muncy, Geissler, Olds & Lowe, PLLC

(57) ABSTRACT

A porous bio-material and a method of preparation thereof. The method includes the following steps. First, a body is formed by mixing a bio-ceramic powder, a water-absorbing natural organic material and a liquid. The water-absorbing natural organic material is selected from the group consisting of carrageenan and agar. Then, the body is partially dried to form a machinable porous bio-material. The sizes of pores and porosity can be tailored by controlling the extent of drying so that the porous bio-material with acceptable strength can be obtained.

19 Claims, 3 Drawing Sheets

BIO-MATERIAL AND METHOD OF PREPARATION THEREOF

This application claims priority of No. 096136125 filed in Taiwan R.O.C. on Sep. 28, 2007 under 35 USC 119, the entire content of which is hereby incorporated by reference.

BACKGROUND OF THE INVENTION

1. Field of Invention

The present invention relates to a porous bio-material that can be implanted into a human body and a method of preparation thereof, and more particularly to a porous bio-material with controllable pores, which is adapted to the human body and has relatively high strength, and a method of preparation thereof.

2. Related Art

Bio-ceramics are frequently made of ceramic particles. The sizes of particles of the typical ceramic powder are usually smaller than 10 microns. When the ceramic particles are stacked together, the size of the pores between the particles is also smaller than 10 microns. The pore in the sintered body may even become smaller. The small pores cannot allow white blood corpuscles to pass through and thus cannot be adapted as the artificial bone material.

One conventional method for implanting big pores into the ceramic material is adding artificial polymeric material (e.g., PMMA, PE, PS or the like) to the ceramic powder to form a body, and then to place the body at a temperature higher than 600 degrees centigrade. At this time, the artificial polymeric material slowly disappears due to the high temperature, and the porous ceramic body is left behind. For this fabrication process, there is a limit for the artificial polymeric material to be added. As the amount of the artificial polymer is higher than the limit, the ceramic body may collapse as the artificial polymeric material is being burned off so that the desired product cannot be obtained. If the amount of the artificial polymeric material is low and the amount of ceramic powder is high, the big pores left behind by removing the artificial polymeric material are usually enclosed by the ceramic powder, and the pores exposed at the surface of porous ceramic are consequently smaller so that the blood cannot easily flow.

Another conventional method for implanting big pores into the ceramic material is mainly to use an artificial polymeric sponge as a template, to coat a ceramic slurry onto the artificial polymeric sponge, and then to burn off the artificial polymeric sponge to a temperature higher than 600 degrees centigrade so that the porous body with porosity over 90% can be obtained. The sizes of the pores formed in this process can reach several millimeters as resulted from the large pores of the sponge. However, the drawback is that the strength of the porous ceramic material is usually low because of its large amount of large pores. Furthermore, because only several sizes of the pores are available for the artificial polymeric sponge, only several sizes for the pores in the porous ceramic material are possible.

SUMMARY OF THE INVENTION

The present invention discloses a porous bio-material and a method of preparation thereof, in which the sizes of pores in the porous bio-material can be advantageously controlled, and the strength and the biomedical affinity of the porous bio-material can be advantageously held. So, the present invention is adapted to the field of the bio-material.

The porous bio-material of the present invention is fabricated by mixing at least one bio-ceramic powder (e.g., calcium phosphate, calcium sulphate and/or calcium carbonate powder) with at least one highly water-absorbing natural organic material (e.g., pectin, carrageenan and/or gelatin) and a liquid to form a mixture, and then drying the mixture to obtain the body. An amount of the highly water-absorbing natural organic material is used to form big pores in the body. The amount of pores can be controlled by controlling the amount of the highly water-absorbing natural organic material and the extent of drying.

The highly water-absorbing natural organic material adopted in the present invention is a food grade organic material, such as ficus awkeotsang or agar, so it can be used in a human body and needs not to be completely removed. The food grade highly water-absorbing natural organic material is soluble in the water. So, it is only necessary to add the bio-ceramic powder to the water with the highly water-absorbing natural organic material to form a mixture, and then dry the mixture to prepare the porous bio-material.

Different amounts of the highly water-absorbing natural organic material can be retained by controlling the extent of drying. If only a smaller amount is retained, the highly water-absorbing natural organic material may serve as a binder to hold the ceramic particles. The dried porous bio-material can still have the handling strength. Regarding the control of the extent of drying, the highly water-absorbing natural organic material releases various amounts of moisture. The more the moisture is released, the more pores are formed. So, the sizes of pores and its content can be tailored by controlling the extent of drying.

The highly water-absorbing natural organic material may be completely burned off at a temperature higher than 600 degrees centigrade so that the porous ceramic material is resulted to serve as the porous bio-material, such as the artificial bone material.

Further scope of the applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

The present invention will become more fully understood from the detailed description given hereinbelow and the accompanying drawings which are given by way of illustration only, and thus are not limitative of the present invention.

DETAILED DESCRIPTION OF THE INVENTION

The present invention will be apparent from the following detailed description, which proceeds with reference to the accompanying drawings, wherein the same references relate to the same elements.

Figure 1:
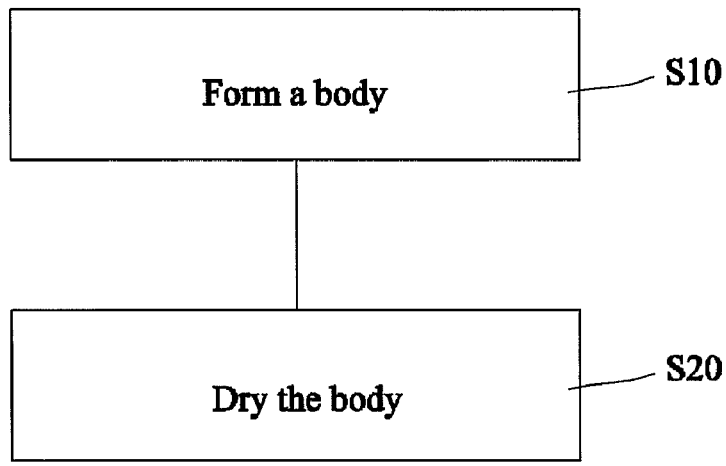
FIG. 1 is a flow chart showing a method of preparing a porous bio-material according to the present invention.
Figure 2:
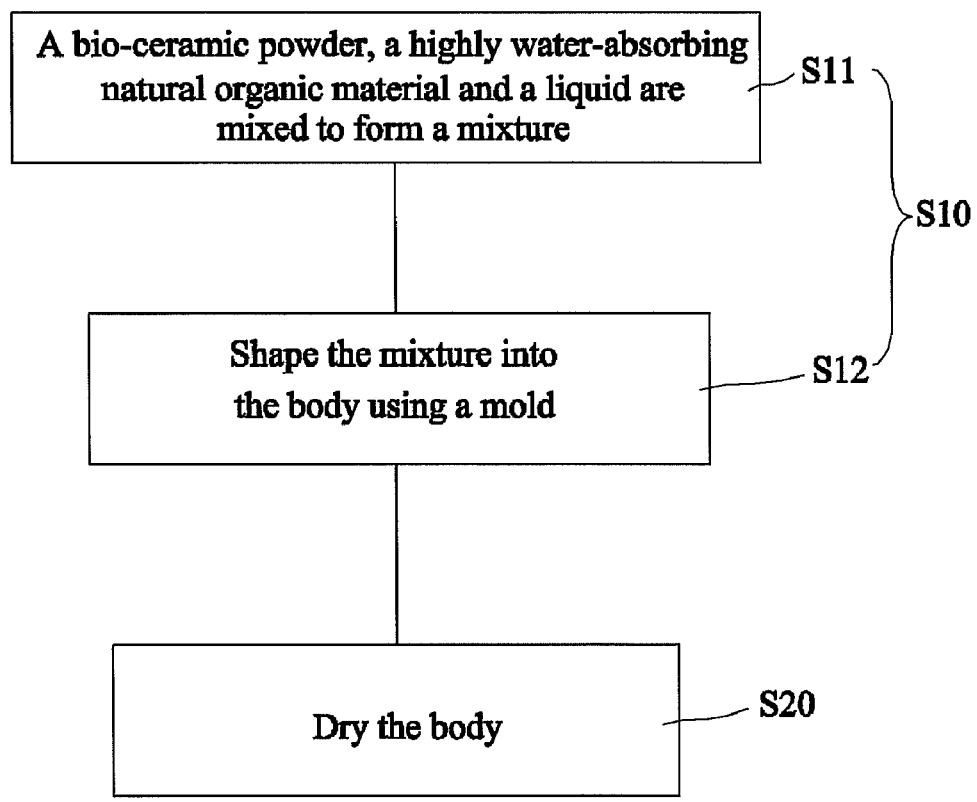
FIG. 2 is a detailed flow chart showing a method of preparing the porous bio-material according to the present invention.

FIG. 1 is a flow chart showing a method of preparing a porous bio-material according to the present invention. Referring to FIG. 1, the method of preparing the porous bio-material according to the present invention includes the following steps. First, in step S10, a body is formed by mixing a bio-ceramic powder, a highly water-absorbing natural organic material and a liquid. Then, in step S20, the body is dried to obtain the porous bio-material. FIG. 2 is a detailed flow chart showing a method of preparing the porous bio-material according to the present invention. As shown in FIG. 2, the step S10 may include steps S11 and S12. In the step S11, the bio-ceramic powder, the highly water-absorbing natural organic material and the liquid are mixed to form a mixture. In the step S12, the mixture is shaped into the body using a mold. That is, the mixture is poured into the mold to form the body, which has the shape of a tooth or a bone in skeleton. The mold may be removed after or before the body is dried. It is to be noted that the step of shaping the mixture by the mold is not essential, and it is also possible to cut a small block from the dried body or to machine the small block.

In the following example, the method of preparing the porous bio-material of the present invention will be described to prove that the method is simple and the porous bio-material has excellent property.

FIRST TO SEVENTH EXAMPLES

In each example, a quantity of bio-ceramic powder (hydroxyapatite powder, a calcium phosphate material), a quantity of highly water-absorbing natural organic powder (agar powder) and a quantity of liquid (deionized water) are uniformly mixed and stirred to form a body. Next, the body is indirectly heated in a hot water for 2 minutes and then poured into a circular polytetrafluoroethylene (PTFE) mold and then cooled. Then, a spherical disc is taken out, placed at the room temperature and in the ventilate environment and then dried for 30 hours. The results are listed in Table 1.

TABLE 1

|  | Hydroxyapatite (%) | Highly water-absorbing natural organic material (%) | Water (%) | Weight loss after being dried (%) |
|---|---|---|---|---|
| First example | 4.34 | 8.65 | 87.0 | 85.0 |
| Second example | 2.32 | 4.68 | 93.0 | 92.2 |
| Third example | 4.46 | 6.66 | 88.9 | 87.7 |
| Fourth example | 9.06 | 0.93 | 90.0 | 88.2 |
| Fifth example | 16.0 | 4.00 | 80.0 | 77.7 |
| Sixth example | 16.37 | 1.66 | 82.0 | 80.0 |
| Seventh example | 8.70 | 4.37 | 86.9 | 85.5 |

According to the above-mentioned examples, the quantity of bio-ceramic powder (hydroxyapatite powder), the quantity of highly water-absorbing natural organic powder (agar powder) and the quantity of deionized water are uniformly mixed to form the body and thus the spherical disc. It represents that the body is machinable. In the above-mentioned examples, the weight of the water is 10 to 100 times that of the agar. So, it represents that the agar can absorb a lot of water and thus has strong water-absorbing ability. If the drying process is then performed, its weight loss is smaller than the weight of the added water. So, it represents that some water is absorbed by the highly water-absorbing natural organic material and that the agar has the excellent water-absorbing ability.

EIGHTH TO FOURTEENTH EXAMPLES

Similar to the first to seventh examples, a quantity of bio-ceramic powder (hydroxyapatite powder), a quantity of highly water-absorbing natural organic powder (agar powder) and a quantity of deionized water are mixed to form a body, and a circular PTFE mold is used to prepare a spherical disc. Next, the disc is removed from the PTFE mold and dried, and then placed into an oven so that the sample can be dried and the variation of the sample can be recorded. In the oven, the temperature is slowly risen to 300 degrees centigrade, and then risen to 1100 degrees centigrade, which is higher than 1000 degrees centigrade, at the speed of 5 degrees centigrade per minute. The temperature of 1100 degrees centigrade is held for one hour, and the measured weight variation and porosity are listed in Table 2.

TABLE 2

|  | Hydroxyapatite (%) | Highly water-absorbing natural organic material (%) | Water (%) | Weight loss after being sintered* (%) | Porosity (%) |
|---|---|---|---|---|---|
| 8th example | 4.3 | 8.7 | 87.0 | 68.4 | 52 |
| 9th example | 2.3 | 4.7 | 93.0 | 62.3 | 48 |
| 10th example | 4.5 | 6.7 | 88.9 | 50.3 | 39 |
| 11th example | 9.1 | 0.9 | 90.0 | 14.2 | 66 |
| 12th example | 16.0 | 4.0 | 80.0 | 25.2 | 72 |
| 13th example | 16.4 | 1.7 | 82.0 | 14.3 | 70 |
| 14th example | 8.7 | 4.4 | 86.9 | 37.5 | 59 |

*The weight loss after being sintered is equal to [(the weight after being dried) − (the weight after sintering)]/(the weight after being dried) * 100%.

According to the above-mentioned examples, the quantity of bio-ceramic powder (hydroxyapatite powder), the quantity of highly water-absorbing natural organic powder (agar powder) and the deionized water are uniformly mixed to form the spherical disc, which can be dried and/or sintered to form the porous bio-ceramic material having the porosity higher than 70%. It represents that the high water-absorbing ability of the agar can be utilized to prepare the porous bio-ceramic material successfully.

FIFTEENTH EXAMPLE

Similar to the first to seventh examples, a quantity of bio-ceramic powder (hydroxyapatite powder), a quantity of highly water-absorbing natural organic powder (agar powder) and a quantity of deionized water are mixed to form a body, and a circular PTFE mold is used to prepare a spherical disc. Then, the spherical disc is taken out of the mold and dried. Next, the upper and lower surfaces of the sample are slighted ground, and a biaxial 4-ball testing method is performed to test the bending strength of the spherical disc, and the tested data are listed in Table 3.

TABLE 3

|  | Hydroxyapatite (%) | Highly water-absorbing natural organic material (%) | Water (%) | Strength (MPa) |
|---|---|---|---|---|
| 15th example | 16.2 | 2.8 | 81 | 11.4 |

According to the above-mentioned example, the porous bio-material is prepared by drying the mixed body of the hydroxyapatite, the agar and the deionized water. A small amount of agar is retained after various extents of drying. The strength of the partial dried body is acceptable due to the presence of the remaining agar. The partial dried body can be machined. Therefore, the addition of the highly water absorbing natural organic material is beneficial to the improvement on the strength of the porous bio-material.

SIXTEENTH TO NINETEENTH EXAMPLES

First, a quantity of bio-ceramic (calcium sulphate) powder, a quantity of highly water-absorbing natural organic powder (agar powder) and a quantity of deionized water are uniformly mixed and stirred to form a body. Next, the body is indirectly heated by the boiling water for 10 minutes and then poured into a circular polytetrafluoroethylene (PTFE) mold and then cooled. Then, a spherical disc is taken out, placed in the ventilate environment and then dried. The results are listed in Table 4. Because the calcium sulphate in the dried spherical disc and the water form the dihydrate calcium sulphate, the theoretical weight loss after being dried is lower than the original water content.

TABLE 4

| | Calcium sulphate powder (%) | Highly water-absorbing natural organic material (%) | Water (%) | Theoretical weight loss of water after being dried (%) | Weight loss after being dried (%) |
|---|---|---|---|---|---|
| $16^{th}$ example | 48.78 | 2.439 | 48.78 | 35.87 | 30.30 |
| $17^{th}$ example | 32.26 | 3.226 | 64.52 | 55.98 | 50.16 |
| $18^{th}$ example | 8.658 | 4.348 | 86.96 | 84.67 | 83.43 |
| $19^{th}$ example | 31.25 | 6.250 | 62.50 | 54.23 | 56.07 |

According to the above-mentioned examples, the quantity of bio-ceramic powder (calcium sulphate powder), the quantity of highly water-absorbing natural organic powder (agar powder) and the quantity of deionized water are uniformly mixed to form the body and then the spherical disc. To be demonstrated later, the body is machinable. In the above-mentioned examples, the weight of the water is 20 to 100 times that of the agar. So, it represents that the agar can absorb a lot of water and thus has strong water-absorbing ability. If the drying process is then performed, its weight loss is smaller than the weight of the added water. So, it represents that some water is absorbed by the highly water-absorbing natural organic material and that the agar has the excellent water-absorbing ability. Twentieth to twenty-third examples Similar to the sixteenth to nineteenth examples, a quantity of bio-ceramic powder (calcium sulphate powder), a quantity of highly water-absorbing natural organic powder (agar powder) and a quantity of deionized water are mixed to form a body, and a circular PTFE mold is used to prepare a spherical disc. Next, the spherical disc is removed from the PTFE mold and dried, and then placed into an oven so that the sample can be heated and dried and the variation of the sample can be recorded. In the oven, the temperature is slowly risen to 300 degrees centigrade, and then risen to 1100 degrees centigrade at the speed of 5 degrees centigrade per minute. The temperature of 1100 degrees centigrade is held for one hour, and the measured weight variation and porosity are listed in Table 5.

TABLE 5

| | Calcium sulphate powder (%) | Highly water-absorbing natural organic material (%) | Water (%) | Weight loss after being sintered* (%) | Porosity (%) |
|---|---|---|---|---|---|
| $20^{th}$ example | 48.78 | 2.439 | 48.78 | 24.07 | 45.91 |
| $21^{st}$ example | 32.26 | 3.226 | 64.52 | 27.15 | 51.25 |
| $22^{nd}$ example | 8.658 | 4.348 | 86.96 | 44.42 | 35.15 |
| $23^{rd}$ example | 31.25 | 6.250 | 62.50 | 32.79 | 35.19 |

*The weight loss after being sintered is equal to [((the weight after being dried) − (the weight after sintering)]/(the weight after being dried) * 100%.

According to the above-mentioned examples, the calcium sulphate powder, the agar powder and the deionized water are uniformly mixed to form the spherical disc, which can be typically dried and/or sintered to form the porous bio-ceramic material having the porosity higher than 50%. It represents that the high water-absorbing ability of the agar can be utilized to prepare the porous bio-ceramic material successfully.

TWENTY-FOURTH AND TWENTY-FIFTH EXAMPLES

Similar to the sixteenth to nineteenth examples, a quantity of bio-ceramic powder (calcium sulphate powder), a quantity of highly water-absorbing natural organic powder (agar powder) and a quantity of deionized water are mixed to form a body, and a circular PTFE mold is used to prepare a spherical disc. Then, the spherical disc is taken out of the mold and dried. Next, the upper and lower surfaces of the sample are slighted ground, and the biaxial 4-ball testing method used in the fifteenth example is performed to test the bending strength of the disc, and the tested data are listed in Table 6.

TABLE 6

| | Calcium sulphate powder (%) | Highly water-absorbing natural organic material (%) | Water (%) | Strength (MPa) |
|---|---|---|---|---|
| $24^{th}$ example | 48.78 | 2.439 | 48.78 | 4.7 |
| $25^{th}$ example | 8.658 | 4.348 | 86.96 | 71.6 |

According to the above-mentioned examples, the porous bio-material prepared by drying the mixed body of the calcium sulphate powder, the agar and the deionized water has the excellent strength. This is because the agar reacts with the water to provide the strength for the porous bio-ceramic material.

TWENTY-SIXTH TO TWENTY-NINTH EXAMPLES

Similar to the sixteenth to nineteenth examples, a quantity of calcium sulphate ceramic powder, a quantity of highly water-absorbing natural agar organic powder and a quantity of deionized water are mixed to form a body, and a circular PTFE mold is used to prepare a spherical disc. Then, the spherical disc is taken out of the mold and dried. Next, the cross section of the sample is ground and then observed with a scanning electron microscope. Then, the image analysis technique is used to analyze the sizes and the distributions of the larger pores on the cross section, and the associated data are listed in Table 7.

TABLE 7

| | Calcium sulphate powder (%) | Highly water-absorbing natural organic material (%) | Water (%) | Average size of pores (microns) |
|---|---|---|---|---|
| 26th example | 19 | 4 | 77 | 170 ± 85 |
| 27th example | 32 | 3 | 65 | 175 ± 68 |
| 28th example | 42 | 2 | 56 | 157 ± 67 |
| 29th example | 49 | 2 | 49 | 125 ± 47 |

Figure 3:
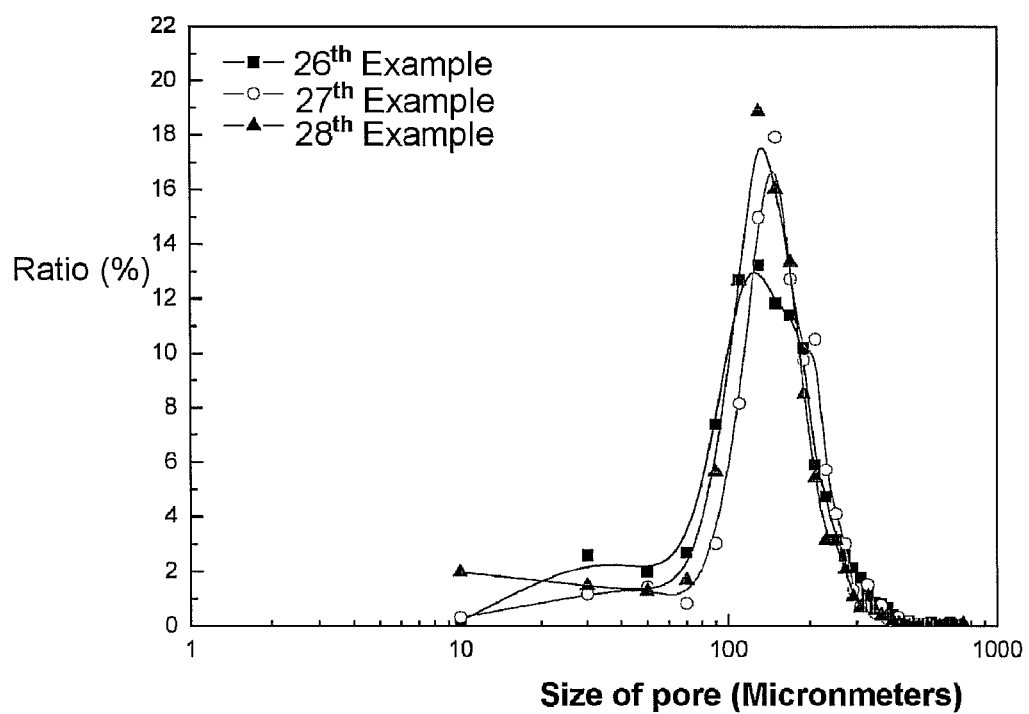
FIG. 3 is a graph showing the size distributions of pores in the ceramics according to twenty-sixth to twenty-eighth examples.

FIG. 3 is a graph showing the size distributions of pores in the ceramics according to the twenty-sixth to twenty-eighth examples. As shown in Table 7 and FIG. 3, it is obtained that the sizes of the pores are greater than 100 microns and the sizes of the pores are relatively uniform, wherein the pores are formed according to the method of the present invention.

THIRTIETH EXAMPLE

Figure 4:
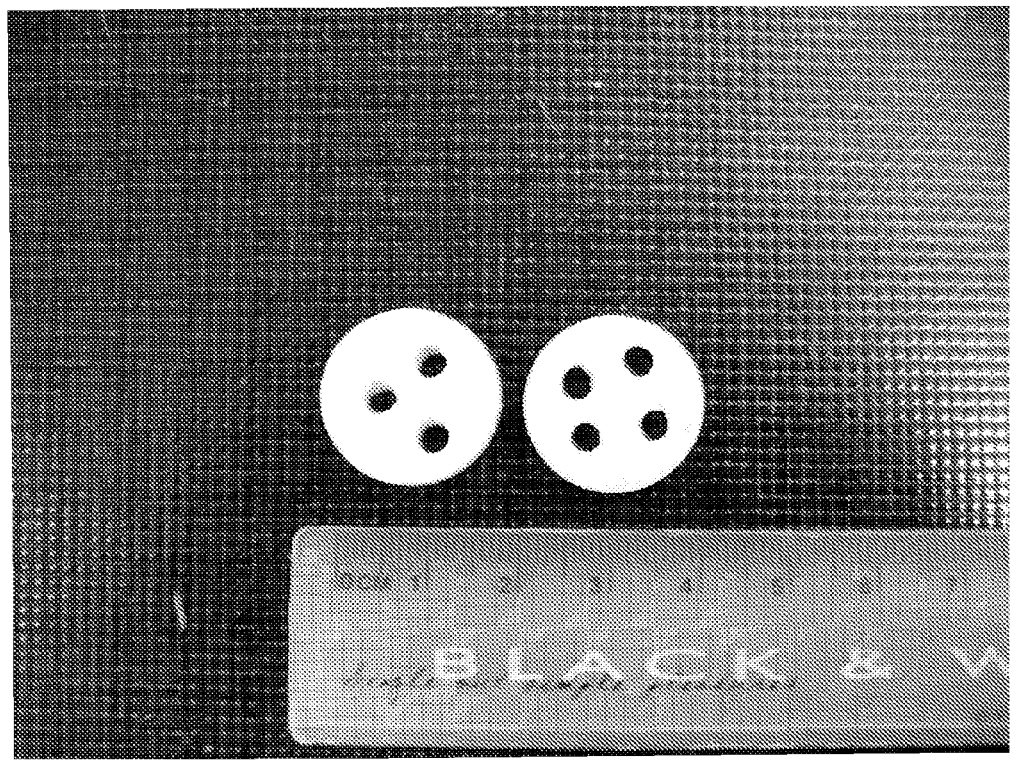
FIG. 4 shows the porous bio-materials fabricated in the ceramic according to the thirty example, wherein the pores are produced using a plastic flexible tube.

Similar to the first to seventh examples, a quantity of bio-ceramic powder (hydroxyapatite powder, or calcium phosphate material), a quantity of highly water-absorbing natural organic powder (agar powder) and a quantity of deionized water are uniformly mixed and stirred to form a body. Then, a spherical disc is prepared using a circular PTFE mold, and the spherical disc is taken out of the mold and dried for ten minutes. Next, a plastic flexible tube is used to produce holes in the center of the spherical disc, as shown in FIG. 4, which illustrates that the body formed of the bio-ceramic powder, the highly water-absorbing natural organic material and the deionized water is machinable.

Thus, the porous bio-material according to the present invention includes a liquid, bio-ceramic powder and a highly water-absorbing natural organic material. The liquid, the bio-ceramic powder and the highly water-absorbing natural organic material are combined together to form a machinable porous structure. Alternatively, the porous bio-material consists of only the liquid, the bio-ceramic powder and the highly water-absorbing natural organic material.

In summary, the porous bio-material with the acceptable strength can be obtained by adjusting the combination of the bio-ceramic powder, the highly water-absorbing natural organic material and water, and by controlling the extent of drying to control the sizes of the pores and the porosity. The presence of pores is essential to the growth of bone. For example, the pore with the size of 1 micron provides the dissolution and enhances cell attachment, the pore with the size of 10 to 100 microns provides the space for mineralization, the pore with the size greater than 100 microns provides the vascularisation and the internal mineralized bone formation, and the pore with the size greater than 200 microns provides the essential requirement for osteoconduction.

In addition, the bio-ceramic powder may be calcium sulphate powder, calcium phosphate powder or calcium carbonate powder. The weight percentage of the bio-ceramic powder in the body ranges from 1% to 80%, and preferably from 2% to 50%. The weight percentage of the highly water-absorbing natural organic material in the body ranges from 0.1% to 20%, and preferably from 0.5% to 10%. The liquid is the deionized water, and the weight percentage of the liquid in the body is greater than or equal to 10 times that of the highly water absorbing natural organic material. After various extents of drying, the liquid in the partial dried body ranges from 20% to 95%, and preferably from 45% to 95%. The drying step may be performed at the room temperature and in the ventilate environment, or in the oven. The porosity in the porous bio-material ranges from 20% to 90%, and preferably from 30% to 80%. The average size of pores in the porous bio-material is greater than 100 microns, and the strength of the porous bio-material may be greater than 4 MPa.

In a special application, the bio-ceramic powder is preferably the calcium sulphate powder because the calcium sulphate may be decomposed in the human body. Consequently, the porous bio-material may be decomposed after the porous bio-material is implanted into the human body. So, it is unnecessary to take the porous bio-material out via a second operation. On the other hand, the formed porous bio-material may have the shape of bone or tooth. When the body is not dried yet, the mold may be provided to shape the body into the shape of bone or tooth. For example, the porous bio-material formed by drying the body may also be machined by way of, for example, cutting, grinding or punching. The machined porous bio-material may also be baked to remove some highly water-absorbing natural organic material and water to form the bio-material that may be applied to the human body or the animal body. Thus, the porous bio-material according to the present invention may have very wide applications.

While the invention has been described by way of examples and in terms of preferred embodiments, it is to be understood that the invention is not limited thereto. To the contrary, it is intended to cover various modifications. Therefore, the scope of the appended claims should be accorded the broadest interpretation so as to encompass all such modifications.

What is claimed is:

1. A method of preparing a porous bio-material, the method comprising the steps of:
    forming a body by mixing a bio-ceramic powder, a water-absorbing natural organic material and a liquid, wherein the water-absorbing natural organic material is selected from the group consisting of carrageenan and agar; and
    drying the body to obtain the porous bio-material.

2. The method according to claim 1, wherein the bio-ceramic powder is calcium sulphate powder.

3. The method according to claim 1, wherein the bio-ceramic powder is calcium phosphate powder or calcium carbonate powder.

4. The method according to claim 1, wherein a weight percentage of the bio-ceramic powder in the body ranges from 1% to 80%.

5. The method according to claim 1, wherein the water-absorbing natural organic material is agar.

6. The method according to claim 1, wherein a weight percentage of the water-absorbing natural organic material in the body ranges from 0.1% to 10%.

7. The method according to claim 1, wherein the liquid is water, and a weight percentage of the liquid is substantially greater than or equal to ten times of a weight percentage of the water-absorbing natural organic material in the body.

8. The method according to claim 1, wherein the step of drying the body is performed at a room temperature.

9. The method according to claim 1, wherein the step of drying the body is performed in an oven, and the step of drying the body is performed at a temperature higher than 600 degrees centigrade.

10. The method according to claim 1, wherein porosity in the porous bio-material ranges from 20% to 90%.

11. The method according to claim 1, wherein an average size of pores in the porous bio-material is greater than 100 microns.

12. The method according to claim 1, wherein the step of forming the body comprises:

forming a mixture by mixing the bio-ceramic powder, the water-absorbing natural organic material and the liquid; and shaping the mixture into the body using a mold.

13. The method according to claim 12, wherein the mold is removed before the step of drying the body.

14. A porous bio-material, comprising:

a liquid;

a bio-ceramic powder; and a water-absorbing natural organic material, wherein the liquid, the bio-ceramic powder and the water-absorbing natural organic material are combined together to form a machinable porous structure, and the water-absorbing natural organic material is selected from the group consisting of carrageenan and agar.

15. The porous bio-material according to claim 14, wherein the bio-ceramic powder is calcium sulphate powder, calcium phosphate powder or calcium carbonate powder.

16. The porous bio-material according to claim 14, wherein the water-absorbing natural organic material is agar.

17. The porous bio-material according to claim 14, wherein the liquid is water, and porosity in the porous bio-material ranges from 20% to 90%.

18. The porous bio-material according to claim 14, wherein an average size of pores of the porous bio-material is greater than 100 microns.

19. The porous bio-material according to claim 14, wherein the porous bio-material consists of the liquid, the bio-ceramic powder and the water-absorbing natural organic material, and the bio-ceramic powder is calcium sulphate powder.

* * * * *